(12) United States Patent
Helgeson et al.

(10) Patent No.: US 11,690,670 B2
(45) Date of Patent: Jul. 4, 2023

(54) ELONGATE MEDICAL DEVICE INCLUDING CHAMFERED RING ELECTRODE AND VARIABLE SHAFT

(71) Applicant: St. Jude Medical, Cardiology Division, Inc., St. Paul, MN (US)

(72) Inventors: Zachary L. Helgeson, Richfield, MN (US); Alexander C. Houck, Hopkins, MN (US); John Her, Brooklyn Park, MN (US); Salo Arias, Maple Grove, MN (US); Somally Mom, Savage, MN (US); Brian M. Monahan, Elk River, MN (US); Neil D. Hawkinson, Ramsey, MN (US); James R. Nigg, Howard Lake, MN (US); James C. Marrs, Arden Hills, MN (US); Xuan Yen Khieu, Maple Grove, MN (US); Troy T. Tegg, Elk River, MN (US); Jill A. LaFavor, Minnetonka, MN (US); Israel A. Byrd, Richfield, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 4 days.

(21) Appl. No.: 17/338,354

(22) Filed: Jun. 3, 2021

(65) Prior Publication Data
US 2021/0369342 A1    Dec. 2, 2021

Related U.S. Application Data

(63) Continuation of application No. 15/116,785, filed as application No. PCT/US2015/014254 on Feb. 3, 2015, now Pat. No. 11,051,878.

(Continued)

(51) Int. Cl.
     *A61B 18/14*      (2006.01)
     *A61B 5/00*      (2006.01)
     (Continued)

(52) U.S. Cl.
     CPC ............ *A61B 18/1492* (2013.01); *A61B 5/01* (2013.01); *A61B 5/021* (2013.01); *A61B 5/283* (2021.01);
     (Continued)

(58) Field of Classification Search
     CPC ..... A61B 34/20; A61B 18/1492; A61B 5/283; A61B 5/6858; A61B 5/01; A61B 5/021;
     (Continued)

(56) References Cited

U.S. PATENT DOCUMENTS

| 3,674,014 A | 7/1972 | Tillander |
| 5,254,107 A | 10/1993 | Soltesz |

(Continued)

FOREIGN PATENT DOCUMENTS

| CN | 103417290 A | 12/2013 |
| EP | 2664295 A1 | 11/2012 |

(Continued)

*Primary Examiner* — Lien M Ngo
(74) *Attorney, Agent, or Firm* — Armstrong Teasdale LLP

(57) ABSTRACT

An elongate medical device shaft may comprise an elongate body and an annular electrode disposed on the elongate body. The annular electrode may define a longitudinal axis and have an outer diameter. The outer diameter may be greater at an axial center of the electrode than at an axial end of the electrode. Additionally or alternatively, the elongate body may comprise three longitudinal sections having three wall thicknesses. The middle wall thickness may be less than the proximal and distal wall thicknesses and the distal wall thickness may be less than the proximal wall thickness. Additionally or alternatively, the shaft may comprise an inner cylindrical structure and an outer tube. The outer tube (Continued)

may comprise a first radial layer and a second radial layer that is radially-outward of the first radial layer, the first radial layer, second radial layer, and inner structure having different stiffnesses.

18 Claims, 10 Drawing Sheets

Related U.S. Application Data

(60) Provisional application No. 61/936,677, filed on Feb. 6, 2014.

(51) Int. Cl.
| | |
|---|---|
| *A61B 5/01* | (2006.01) |
| *A61B 5/021* | (2006.01) |
| *A61B 5/283* | (2021.01) |
| *A61B 34/20* | (2016.01) |
| *A61B 18/00* | (2006.01) |
| *A61M 25/01* | (2006.01) |
| *A61M 25/00* | (2006.01) |
| *A61B 18/16* | (2006.01) |
| *A61B 5/318* | (2021.01) |

(52) U.S. Cl.
CPC ............ *A61B 5/6858* (2013.01); *A61B 34/20* (2016.02); *A61B 5/318* (2021.01); *A61B 5/6859* (2013.01); *A61B 2018/00029* (2013.01); *A61B 2018/00059* (2013.01); *A61B 2018/00166* (2013.01); *A61B 2018/00267* (2013.01); *A61B 2018/00351* (2013.01); *A61B 2018/00577* (2013.01); *A61B 2018/00791* (2013.01); *A61B 2018/00839* (2013.01); *A61B 2018/00892* (2013.01); *A61B 2018/1405* (2013.01); *A61B 2018/1465* (2013.01); *A61B 2018/1467* (2013.01); *A61B 2018/1475* (2013.01); *A61B 2018/165* (2013.01); *A61B 2018/167* (2013.01); *A61B 2034/2051* (2016.02); *A61M 25/0013* (2013.01); *A61M 25/0023* (2013.01); *A61M 25/0138* (2013.01); *A61M 25/0147* (2013.01); *A61M 25/0158* (2013.01)

(58) Field of Classification Search
CPC .................. A61B 5/318; A61B 5/6859; A61B 2018/00166; A61B 2018/1467; A61B 2018/1475; A61B 2018/167; A61M 25/0158; A61M 25/0147; A61M 25/0138; A61M 25/0013
USPC ........... 606/32–41, 47–50; 604/95.04, 95.05, 604/103.06; 600/372–374, 382; 222/93
See application file for complete search history.

(56) References Cited

U.S. PATENT DOCUMENTS

| | | | |
|---|---|---|---|
| 5,354,297 A | 10/1994 | Avitall | |
| 5,542,924 A | 8/1996 | Snoke et al. | |
| 5,715,817 A * | 2/1998 | Stevens-Wright | ........................... A61M 25/0147 604/95.04 |
| 5,782,760 A | 7/1998 | Schaer | |
| 5,938,694 A * | 8/1999 | Jaraczewski | ........... A61B 5/287 607/122 |
| 6,030,369 A | 2/2000 | Engelson et al. | |
| 6,066,125 A | 5/2000 | Webster | |
| 6,233,476 B1 | 5/2001 | Strommer et al. | |
| 6,356,791 B1 | 3/2002 | Westlund et al. | |
| 6,408,199 B1 | 6/2002 | Goldin | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 6,980,843 B2 | 12/2005 | Eng et al. | |
| 7,197,354 B2 | 3/2007 | Sobe | |
| 7,263,397 B2 | 8/2007 | Hauck et al. | |
| 7,300,438 B2 | 11/2007 | Falwell et al. | |
| 7,331,958 B2 * | 2/2008 | Falwell | ............... A61B 18/1492 604/95.04 |
| 7,386,339 B2 | 6/2008 | Strommer et al. | |
| 7,536,218 B2 | 5/2009 | Govari et al. | |
| 7,885,707 B2 | 2/2011 | Hauck | |
| 8,000,764 B2 * | 8/2011 | Rashidi | ............... A61B 18/1492 606/41 |
| 8,187,267 B2 | 5/2012 | Pappone et al. | |
| 8,506,562 B2 | 8/2013 | Anderson et al. | |
| 8,734,440 B2 | 5/2014 | Wu | |
| 9,731,099 B2 | 8/2017 | Krolik et al. | |
| 2003/0045831 A1* | 3/2003 | Ponzi | ................. A61M 25/0144 604/95.04 |
| 2003/0208198 A1 | 11/2003 | Hayzelden et al. | |
| 2006/0020256 A1 | 1/2006 | Bell et al. | |
| 2006/0122514 A1 | 6/2006 | Byrd et al. | |
| 2007/0043390 A1 | 2/2007 | Neilan | |
| 2008/0161774 A1* | 7/2008 | Hastings | .............. A61M 25/005 604/524 |
| 2009/0012517 A1 | 1/2009 | de la Rama et al. | |
| 2009/0149848 A1* | 6/2009 | Werneth | ................ A61B 18/18 606/41 |
| 2009/0281535 A1 | 11/2009 | Truckai et al. | |
| 2010/0076426 A1* | 3/2010 | de la Rama | ......... A61B 5/0036 606/41 |
| 2010/0152731 A1 | 6/2010 | de la Rama et al. | |
| 2012/0029504 A1 | 2/2012 | Afonso et al. | |
| 2012/0041419 A1 | 2/2012 | Blanchard et al. | |
| 2012/0232496 A1 | 9/2012 | Lareau et al. | |
| 2012/0330354 A1 | 12/2012 | Kane et al. | |
| 2013/0066193 A1 | 3/2013 | Olson et al. | |
| 2013/0296780 A1 | 11/2013 | Tegg | |
| 2014/0228820 A1 | 8/2014 | Blaskowski et al. | |

FOREIGN PATENT DOCUMENTS

| | | |
|---|---|---|
| EP | 2679190 A1 | 1/2014 |
| JP | H09140803 A | 6/1997 |
| JP | H11514250 A | 12/1999 |
| JP | 2007282678 A | 11/2007 |
| JP | 2009268696 A | 10/2008 |
| JP | 2012034852 A | 2/2012 |
| JP | 2002119489 A | 4/2012 |
| JP | 2012130702 A | 7/2012 |
| JP | 2012196389 A | 10/2012 |
| JP | 2013533065 A | 8/2013 |
| JP | 2013208429 A | 10/2013 |
| JP | 2014004368 A | 1/2014 |
| JP | 2014018531 A | 2/2014 |
| WO | 1996036277 A1 | 11/1996 |
| WO | 02087676 A2 | 11/2002 |
| WO | 2007/121005 A1 | 10/2007 |
| WO | 2012019225 A1 | 2/2012 |

\* cited by examiner

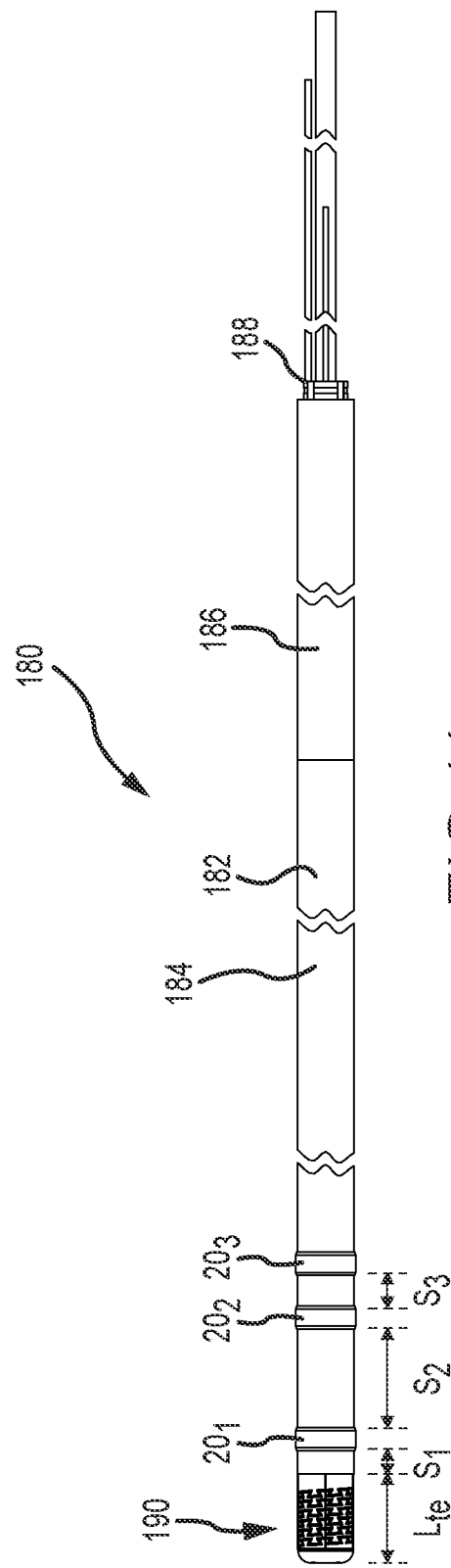

ELONGATE MEDICAL DEVICE INCLUDING CHAMFERED RING ELECTRODE AND VARIABLE SHAFT

CROSS-REFERENCE TO RELATED APPLICATIONS

This application continuation of U.S. application Ser. No. 15/116,785, filed 4 Aug. 2016 (the '785 application), which is a national stage filing based upon international application no. PCT/US2015/014254, filed 3 Feb. 2015 (the '254 application), which claims the benefit of U.S. provisional application No. 61/936,677, filed 6 Feb. 2014 (the '677 application). The '785 application, the '254 application, and the '677 application are all hereby incorporated by reference in their entirety as though fully set forth herein.

BACKGROUND a. Technical Field

The instant disclosure relates to elongate medical devices, including the configuration of the shaft body and of electrodes disposed in or on the shaft body.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter may include a number of features for navigation and guidance of the catheter and for therapy once the catheter is guided to a target site.

The catheter typically carries one or more electrodes, which may be used for ablation, diagnosis, or the like, and/or other sensors. For example, a number of electrodes may be placed on the distal tip and/or outside of the shaft. The electrodes may be used, for example, in navigation with an electrical impedance-based navigation system, to collect electrophysiology data from the heart, and/or to apply ablation energy.

The catheter may also include a number of features enabling the catheter to be steered by a clinician. For example, one or more deflection rings may be embedded in or otherwise coupled with the shaft of the catheter, and additionally coupled with one or more deflection wires that extend through the shaft and are coupled with a deflection mechanism in the handle of the catheter. The deflection ring(s) and deflection wire(s) may be placed in the shaft in a configuration to effect deflection of a desired section of the shaft along a desired shape.

To assist in guiding the catheter to a target site, an introducer may first be guided along a portion of the path to be traveled by the catheter. The catheter may then be passed through a central lumen of the introducer. Like the catheter, the introducer may have electrodes, other sensors, deflection rings and wires, and/or other deflection features for use in navigation and guidance.

The foregoing discussion is intended only to illustrate the present field and should not be taken as a disavowal of claim scope.

BRIEF SUMMARY

An embodiment of an elongate medical device assembly may comprise an elongate shaft body and an annular electrode disposed on the elongate body. The annular electrode may define a longitudinal axis and have an outer diameter. The outer diameter may be greater at an axial center of the electrode than at an axial end of the electrode.

An embodiment of an elongate medical device assembly may comprise an elongate shaft body defining a longitudinal axis. The elongate body may comprise a first longitudinal section defining a first wall thickness, a second longitudinal section defining a second wall thickness, and a third longitudinal section defining a third wall thickness. The second longitudinal section may be distal of the first longitudinal section and the third longitudinal section may be distal of the second longitudinal section. The second wall thickness may be less than the first wall thickness and less than the third wall thickness. The first wall thickness may be greater than the third wall thickness.

An embodiment of an elongate medical device assembly may comprise an elongate shaft comprising an inner cylindrical structure, the inner cylindrical structure defining a longitudinal lumen and defining a longitudinal axis. The elongate shaft may further comprise an outer tube, disposed radially-outward of the inner cylindrical structure. The outer tube may comprise a first radial layer and a second radial layer that is radially-outward of the first radial layer, the first radial layer having a different stiffness than the second radial layer, and both the first and second radial layers having different stiffnesses than the inner cylindrical structure.

BRIEF DESCRIPTION OF THE DRAWINGS

FIG. 11 is a plan view of a portion of an exemplary embodiment of a catheter illustrating, among other features, exemplary electrode spacing.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
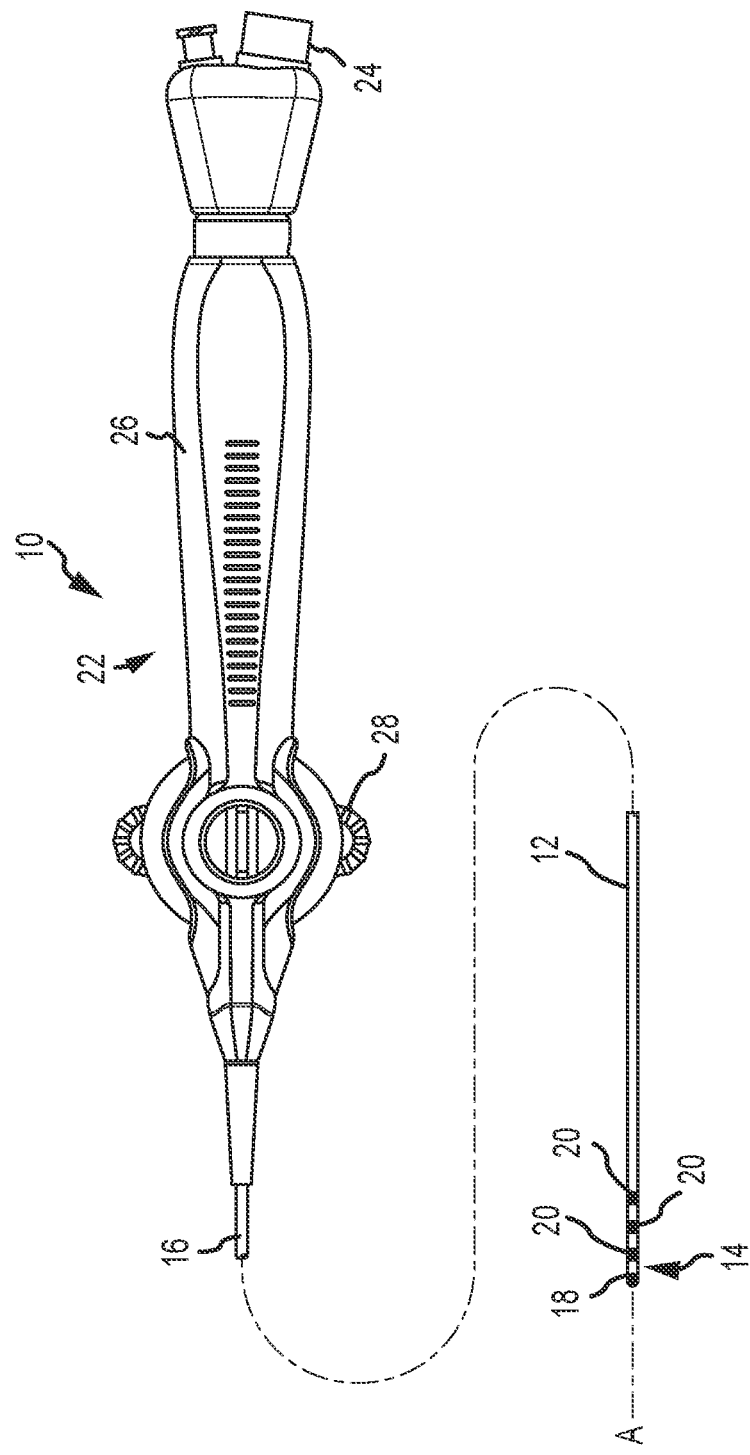
FIG. 1 is a plan view of an exemplary embodiment of a catheter.

Referring now to the figures, in which like numerals indicate the same or similar elements in the various views, FIG. 1 is a plan view of an exemplary embodiment of a catheter 10. The catheter 10 may include an elongate tubular shaft 12 defining a longitudinal axis A and having a distal end portion 14 and a proximal end portion 16, a tip electrode 18, a number of annular ring electrodes 20, and a handle 22 coupled with the catheter shaft 12. The handle 22 may include one or more electromechanical connectors 24 configured to allow the catheter 10, and the electrodes 18, 20 thereof, in particular, to be coupled with components or subsystems of, for example, an electrophysiology (EP) laboratory system. Such components or subsystems may comprise, for example and without limitation, a visualization, navigation, and/or mapping system, an EP monitoring and recording system (e.g., for monitoring and/or recording electrocardiograms (EGM), cardiac signals, etc.), a tissue contact sensing system, an ablation system, a cardiac stimulation system (i.e., EP stimulator), and the like. An exemplary system is shown in U.S. patent application publication no. 2012/0029504, which is hereby incorporated by reference in its entirety as though fully set forth herein.

The shaft 12 may comprise an elongate body defining an axis A. The elongate body may include one or more lumens, for example, for the transmission of fluid, routing of electrical infrastructure for the electrodes 18, 20 and/or other sensors and electrical components, routing of pull wires and shape memory wires, and other purposes. The shaft 12 may comprise one or more polymer, metal, and other layers, and may include additional structures known in the art. In an embodiment, the shaft 12 may include one or more features shown in and described with respect to FIGS. 9 and 10.

In addition to and/or instead of one or more electrodes 18, 20, the catheter 10 may be equipped with one or more additional types of sensors. For example, the catheter 10 may be equipped with one or more coil sensors, temperature sensors, pressure sensors, and/or other sensors. In an embodiment, one or more of the ring electrodes 20 and the tip electrode 18 on the catheter 10 may be configured with one or more of the atraumatic features shown and described herein, in an embodiment.

The handle 22 may be disposed at the proximal end portion 16 of the shaft 12. The handle 22 may provide a location for a clinician to hold the catheter 10 and may further provide means for steering or guiding the shaft 12 within the body of a patient.

The handle 22 may comprise a housing 26. The housing 26 may be of a unitary construction or may be constructed of a plurality of pieces that are configured to be assembled together. In a multi-piece embodiment, the housing 26 may be coupled together in any number of ways known in the art, such as, for example, by press fit or interference coupling techniques, by complementary interlocking members, by conventional fasteners or adhesives, or any other techniques known in the art.

In an exemplary embodiment, the catheter 10 may further comprise a deflection mechanism 28 associated with the handle 22 of the catheter 10. The deflection mechanism 28 may be coupled with a pull assembly disposed at or in the distal end portion 14 of the shaft 12 via one or more deflection wires, which may be rounded, flat, or in some other configuration. The combination of the deflection mechanism 28 and the pull assembly may provide a means by which a user or physician can effect movement (e.g., deflection) of the distal end portion 14 in one or more directions, and therefore, allows the physician to steer the catheter shaft 12. The catheter 10 may further include, in an embodiment, shape memory wires and/or other structure to assist in guiding or shaping the shaft 12.

Figure 2:
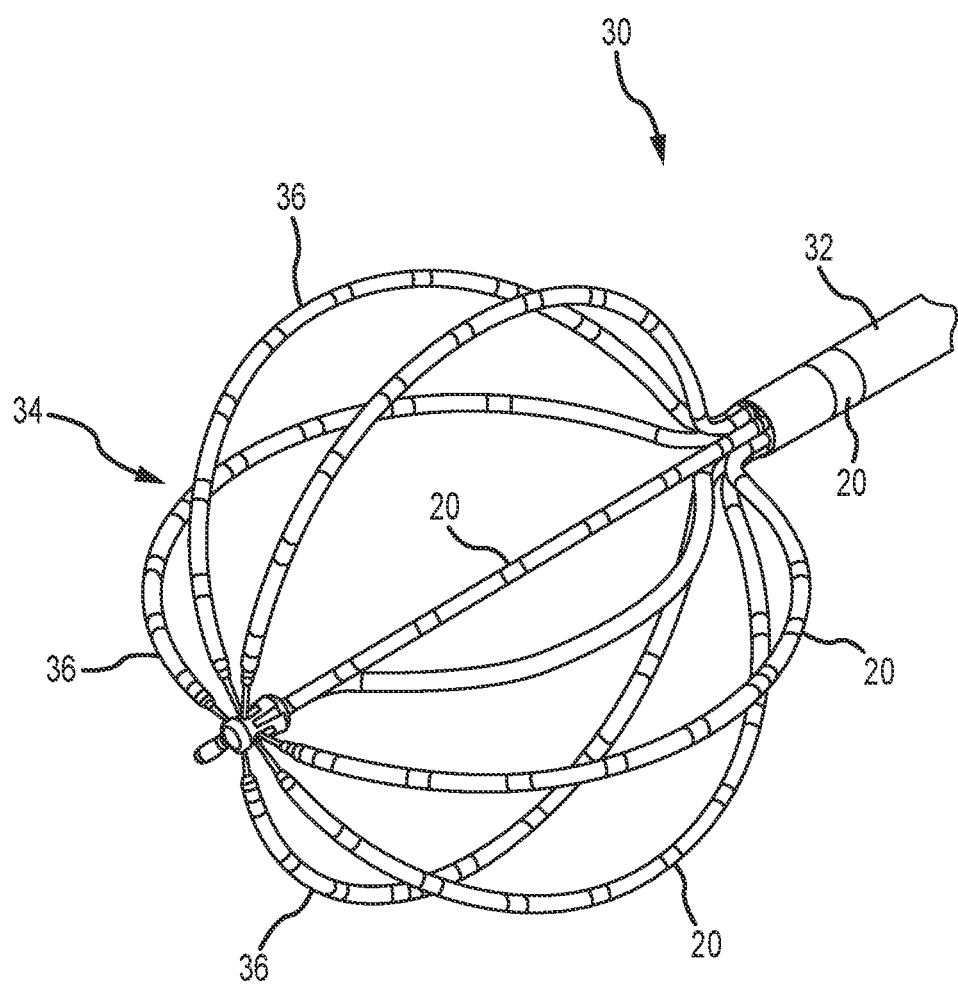
FIG. 2 is an isometric view of a distal end portion of an exemplary embodiment of a basket-style catheter.

FIG. 2 is an isometric view of a distal end portion of an exemplary embodiment of a basket-style catheter 30. The basket-style catheter 30 may include a distal end portion 32 of an elongate shaft having a first annular ring electrode 20 and a basket assembly 34. The distal end portion 32 of the shaft and the basket assembly 34 may be provided in connection with a shaft and handle similar to those shown in and described in conjunction with FIG. 1 (i.e., shaft 12 and handle 22), in an embodiment.

The basket assembly 34 may include a plurality of spines 36, each of which may include a plurality of annular ring electrodes 20, in an embodiment. Not all spines 36 or ring electrodes 20 are designated in FIG. 2 for clarity of illustration. The spines 36 may be flexible. For example, the spines 36 of the basket assembly 34 may collapse for guidance through an introducer, and expand once the basket assembly 34 extends from the distal end of the introducer. The basket-style catheter 30 may be used for a electrophysiological mapping operation, for example. Each of the electrodes 20 on the basket-style catheter 30 may be configured with one or more of the atraumatic features shown and described herein, in an embodiment.

Figure 3:
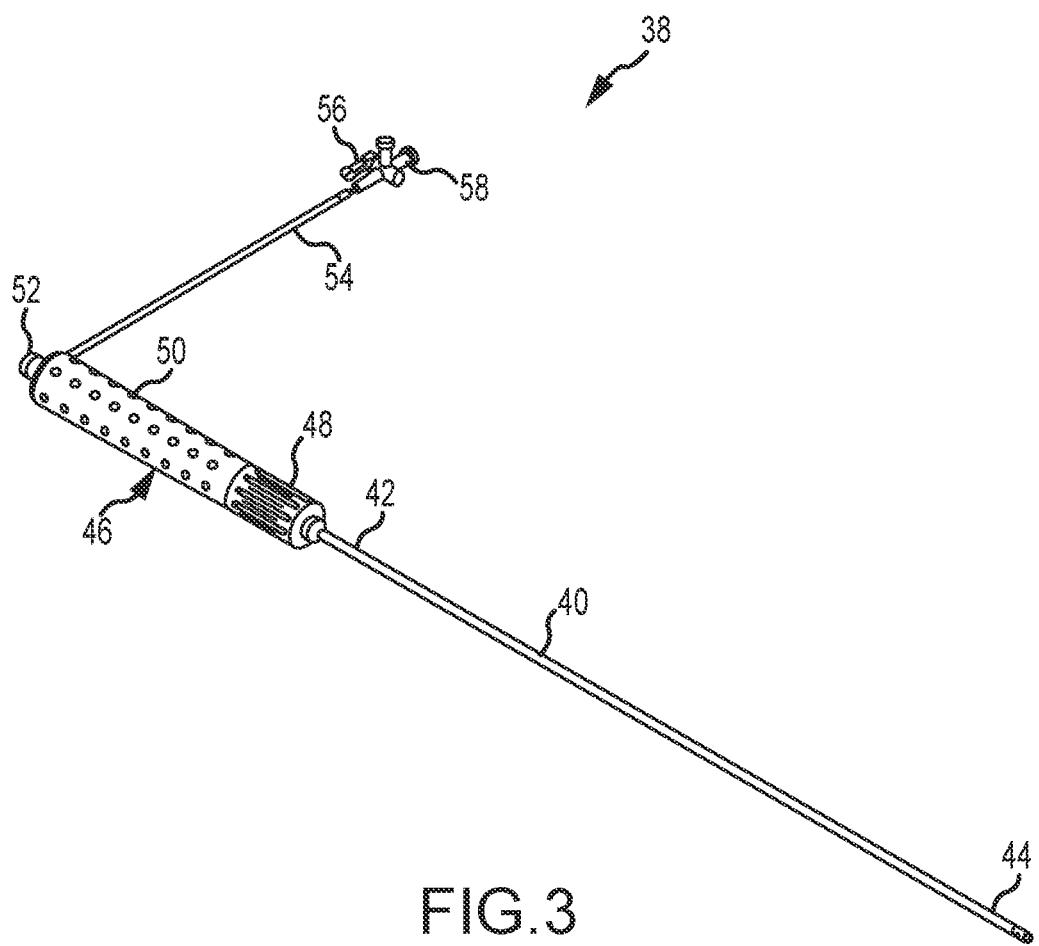
FIG. 3 is a plan view of an exemplary embodiment of an introducer.

FIG. 3 is an isometric view of an exemplary embodiment of an introducer 38. The introducer 38 may be used in conjunction with the catheter 10 of FIG. 1 or the basket-style catheter 30 of FIG. 2. In an exemplary embodiment, the introducer 38 may include a shaft 40 having a proximal end portion 42 and a distal end portion 44, a handle assembly 46 including an adjustment knob 48 and a grip portion 50, a hemostasis valve 52 for insertion of an internal coaxial medical device such as a catheter, and an exterior fluid lumen 54 terminating in a stopcock 56, which may also include a luer taper 58 for connection to an irrigation system (not shown). The introducer may further include other conventional components such as, for example and without limitation, one or more position sensors, a temperature sensor, additional sensors or electrodes, ablation elements (e.g., ablation tip electrodes for delivering RF ablative energy, high intensity focused ultrasound ablation elements, etc.), and corresponding conductors or leads. Additionally, the shaft 40 may include one or more fluid lumens extending from the distal end portion 44 to the proximal end portion 42 (and, in an embodiment, into and though the handle assembly for fluid coupling with the exterior fluid lumen 54) for the delivery and/or removal of one or more fluids such as, for example only, irrigation fluids, bodily fluids, and cryogenic ablation fluids. The introducer may be substantially similar to or the same as one or more introducer embodiments illustrated and/or described in U.S. patent application Ser. No. 13/765,128, filed Feb. 12, 2013, which is hereby incorporated by reference in its entirety as though fully set forth herein.

The shaft 40 may also include one or more pull wires (which may have a round, flat, or other configuration) for deflecting a portion of the shaft 40 such as, for example, the distal end portion 44. Each pull wire may extend through the shaft 40 and be coupled with a pull ring within the shaft 40 or may otherwise be directly or indirectly attached to a portion of the shaft 40 where deflection is desired. Each pull wire may extend through the shaft 40 to the handle assembly 46. Disposed within the shaft may also be one or more additional or alternative deflection elements, including shape memory wires.

The handle assembly 46 is provided to enable a clinician to guide the distal end portion 44 of the shaft 40 to a target site, such as a location within the heart, to allow another medical device, such as a catheter (e.g., the catheter 10 of FIG. 1, a basket-style catheter 30 as shown in FIG. 2, etc.) to be passed through the introducer 38 to perform a particular diagnostic and/or therapeutic function. Accordingly, the handle assembly 46 may be coupled with the proximal end portion 42 of the shaft 40 and may comprise an adjustment knob 48 and a grip portion 50. The grip portion 50 may be configured in size, shape, and materials to be comfortably and securely gripped by a clinician guiding the introducer 38. The adjustment knob 48 may be provided as an exterior mechanism through which a clinician can deflect the shaft 40 such as, for example, the distal end portion 44 of the shaft 40. The adjustment knob 48 may thus be coupled, directly or indirectly, with one or more pull wires that extend through the shaft 40.

In an embodiment, the handle assembly 46 may be omitted from the introducer. In such an embodiment, the shaft 40 may terminate (i.e., on its proximal end) in a stopcock 56, which may also include a luer taper 58 for connection to an irrigation system (not shown), and the proximal electrode 22. Accordingly, in different embodiments, the proximal electrode may be coupled directly to the proximal end portion of the shaft 40 or indirectly to the proximal end portion of the shaft 40, such as through a handle assembly 46, a luer taper 58, or another structure.

Figure 4:
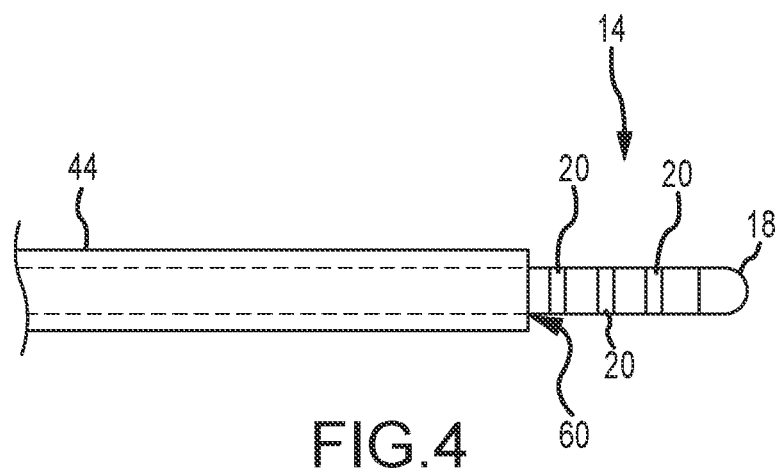
FIG. 4 is a diagrammatic view of a distal end portion of the catheter of FIG. 1 extending through the distal end portion of the introducer of FIG. 3.

FIG. 4 is a diagrammatic view of the distal end portion 14 of the catheter 10 extending from the distal end portion 44 of the introducer 38. In an embodiment, the outer surface of the catheter shaft, including the outer surface of the electrodes 18, 20, may interact with a surface of a lumen 60 of the introducer 38. In an embodiment, the lumen 60 of the introducer 38 may comprise a polymer material, for example. As a result, in some known introducers and catheters, an edge of an electrode 18, 20 on the catheter may scrape material from the introducer lumen 60 as the catheter is advanced through or retracted from the introducer 38. Accordingly, in an embodiment, one or more electrodes 18, 20 on the shaft of the catheter (or on a basket assembly, shaft, and/or other structure on the basket catheter of FIG. 2 or another elongate medical device) may be configured with one or more features of this disclosure to prevent damage to an introducer lumen 60. Electrodes for elongate medical devices and for other devices, more generally, may be configured according to the present disclosure for providing an atraumatic outer surface.

Figure 5B:
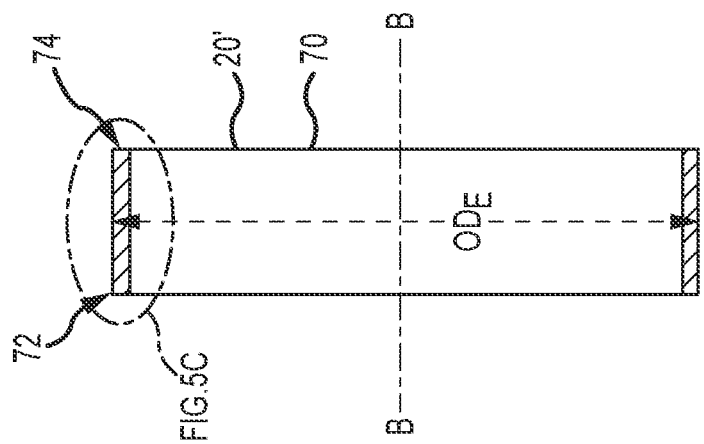
FIGS. 5A-5C are various views of an exemplary embodiment of an annular electrode having rounded ends.
Figure 5C:
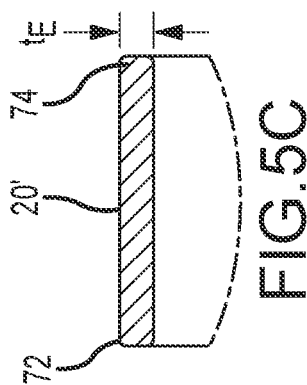
Figure 5A:
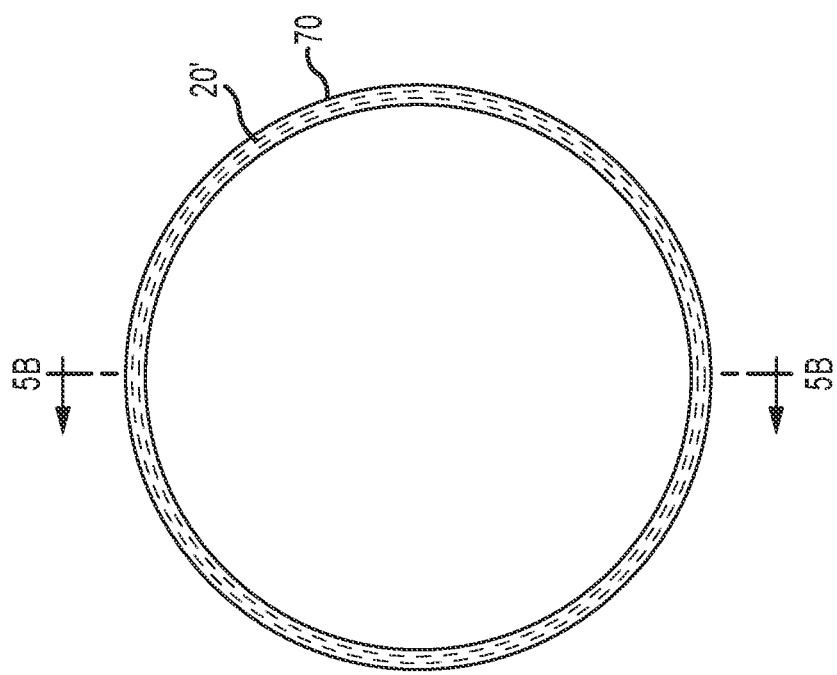

FIG. 5A is an end view of a first embodiment of an atraumatic annular electrode 20'. FIG. 5B is a cross-sectional view of the electrode 20' taken along line 5B-5B in FIG. 5A. FIG. 5C is an enlarged view of a portion of FIG. 5B. The electrode 20' may have a generally annular body 70 defining an axis B a thickness $t_E$, and an outer diameter $OD_E$. The body 70 may also have a first end 72 and a second end 74. The ends 72, 74 of the electrode 20' may have rounded edges that extend around the entire circumference of the electrode 20' in an embodiment. The ends 72, 74 of the electrode 20' may be rounded, for example, by grinding, cutting, sanding, and/or any other method. In an embodiment, the entirety of each end 72, 74 (i.e., both the radially-inward edge and the radially-outward edge) of the electrode 20' may be rounded, as illustrated in FIGS. 5A-5C. In an alternative embodiment, only a single end 72, 74 of the electrode 20' may have rounded edges, and/or only a single edge of an end 72, 74 may be rounded. As a result of the rounded edges of the ends 72, 74 of the electrode 20', the outer diameter $OD_E$ and/or thickness $t_E$ of one or both of the ends 72, 74 of the electrode 20' may be less than the outer diameter $OD_E$ of the axial center of the electrode.

Figure 6B:
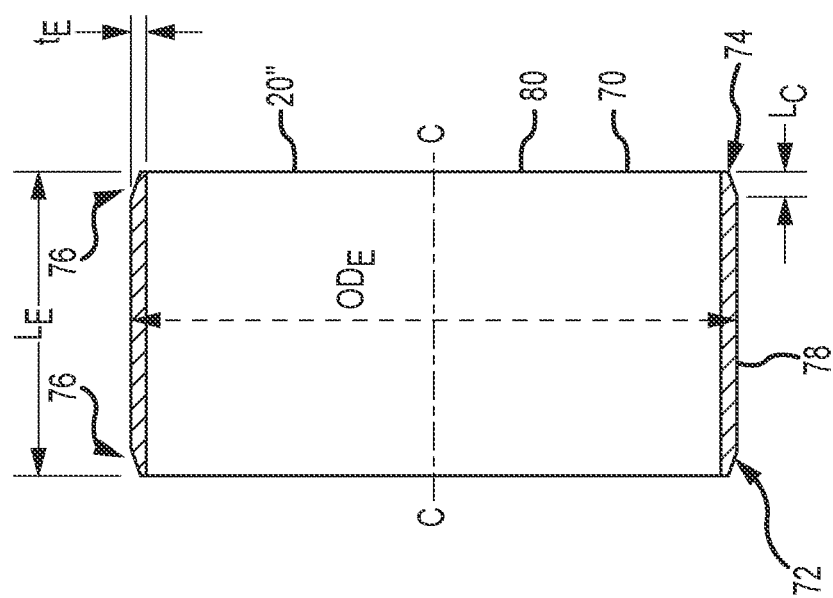
FIGS. 6A-6B are views of an exemplary embodiment of an annular electrode having partially-chamfered ends.
Figure 6A:
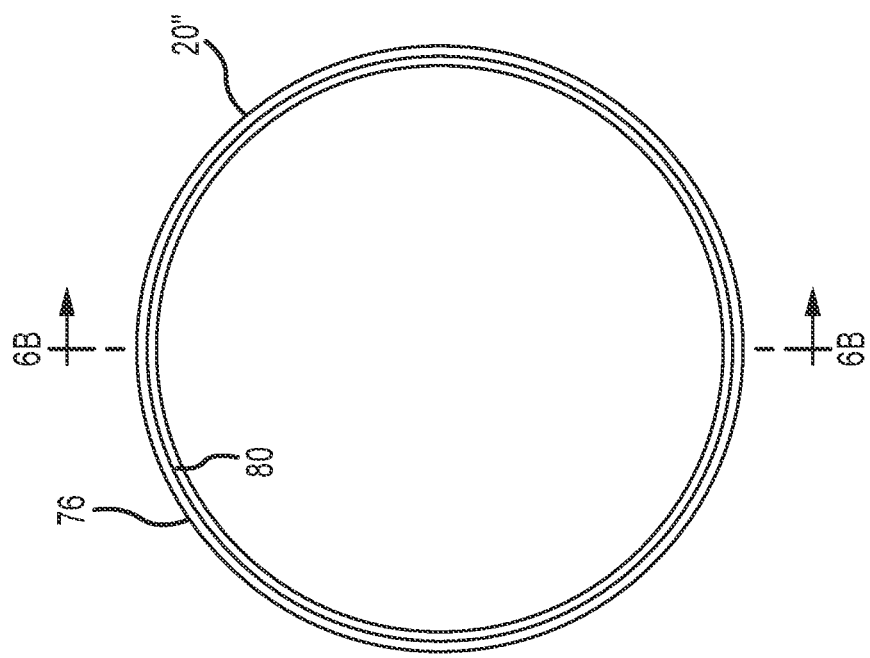

FIG. 6A is an end view of a second embodiment of an atraumatic annular electrode 20". FIG. 6B is a cross-sectional view of the electrode 20" taken along line 6B-6B in FIG. 6A. The electrode may have a generally annular body 70 defining an axis C, a length $L_E$, and a thickness $t_E$. The electrode length $L_E$ may be, for example and without limitation, between about one (1) millimeter and about 1.3 millimeters. The electrode 20" may also have a first end 72 and a second end 74. In an embodiment, both ends 72, 74 of the electrode 20" may include a chamfer 76 that extends around the entire circumference of the electrode 20". Alternatively, only one end 72, 74 of the electrode 20" may include a chamfer 76. In yet another alternative, a chamfer 76 may extend around only a portion of the circumference of the electrode 20". A chamfer 76 may extend from an outer longitudinal surface 78 of the electrode 20" to a radial surface 80 of the electrode 20". Each chamfer 76 may be a partial chamfer 76—i.e., may extend over less than the full thickness $t_E$ of the electrode body 70. The chamfer 76 may extend at any suitable angle and, thus, may have any suitable length $L_C$. Due to a chamfer 76, one or both of the ends 72, 74 of the electrode 20″ may have a lower thickness $t_E$ and/or a lower outer diameter $OD_E$ than the axial center of the electrode 20″.

Figure 7A:
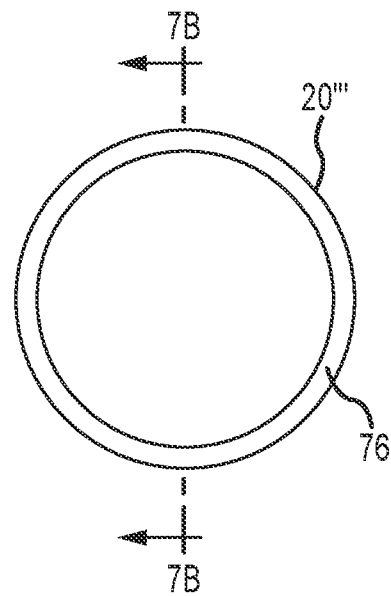
FIGS. 7A-7B are views of an exemplary embodiment of an annular electrode having fully-chamfered ends.
Figure 7B:
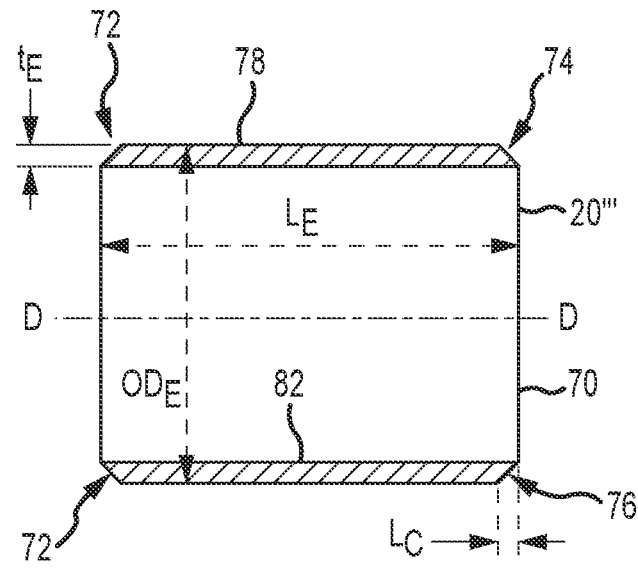

FIG. 7A is an end view of a third embodiment of an atraumatic annular electrode 20‴. FIG. 7B is a cross-sectional view of the electrode 20‴ taken along line 7B-7B in FIG. 7A. The electrode 20‴ may have a generally annular body 70 defining an axis D, a length $L_E$, and a thickness $t_E$. The electrode length $L_E$ may be, for example and without limitation, between about one (1) millimeter and about 1.3 millimeters. The electrode 20‴ may also have a first end 72 and a second end 74. The ends 72, 74 of the electrode 20‴ may each include a chamfer 76′, in an embodiment. Each chamfer 76′ may be a full chamfer 76′, in an embodiment—i.e., the chamfer 76′ may extend from an outer longitudinal surface 78 of the electrode 20‴ over the full thickness $t_E$ of the electrode body 70 to an inner longitudinal surface 82. The full chamfer 76′ may extend at any suitable angle and, thus, may have any suitable length $L_C$. Due to the chamfer 76′, the electrode 20‴ may have a lower thickness $t_E$ and/or outer diameter $OD_E$ at each end 72, 74 than at the axial center of the electrode 20‴.

The chamfers 76, 76′ of the electrodes 20″, 20‴ of FIGS. 6A-7B may be formed by grinding, cutting, and/or any other method. Further, following the removal of material to form the chamfer 76, 76′, the edges transitioning the chamfer 76, 76′ to other surfaces of the electrode 20″, 20‴ may be de-burred, in an embodiment.

Figure 8:
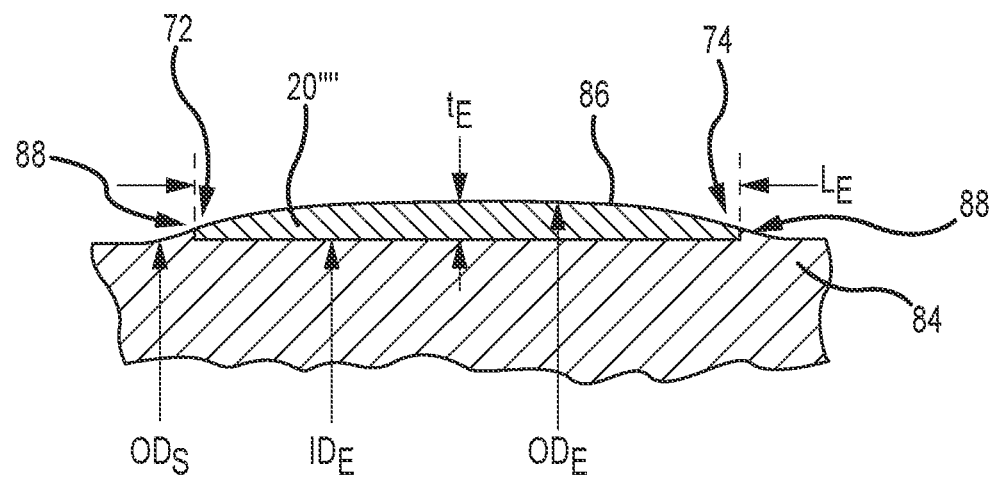
FIG. 8 is a cross-sectional view of an exemplary embodiment of an electrode swaged inside of the outer diameter of an exemplary shaft portion.

FIG. 8 is a diagrammatic cross-sectional view of a fourth embodiment of an atraumatic annular electrode 20″″ disposed on an elongate medical device shaft 84. The electrode 20″″ may have a generally annular body 70 defining an axis (not shown—extending in the plane of the page), a length $L_E$, and a thickness $t_E$. The electrode 20″″ may also have a first end 72 and a second end 74. The outer surface 86 of the electrode body 70 may be continuously curved and, as a result, the thickness $t_E$ and outer diameter $OD_E$ of the electrode may be continuously variable over the length $L_E$ of the electrode body 70, and may be lower at the ends 72, 74 of the electrode 20″″ than at the axial center of the electrode 20″″.

The ends 72, 74 of the electrode 20″″ may be within the threshold of the outer diameter of the shaft $OD_S$, in an embodiment, providing an atraumatic transition from the shaft 84 to the electrode 20″″. For example, in an embodiment, both the inner diameter $ID_E$ and the outer diameter $OD_E$ of one or both ends 72, 74 of the electrode 20″″ may be within the threshold of the outer diameter $OD_S$ of the shaft 84. Alternatively, only the inner diameter $ID_E$, and not the outer diameter $OD_E$, of one or both ends 72, 74 of the electrode 20″″ may be within the threshold of the outer diameter $OD_S$ of the shaft 84. A portion 88 of the shaft 84 (i.e., encompassed by the shaft outer diameter) may extend over and cover the ends of the electrode, in an embodiment, as shown in FIG. 8. Accordingly, the outer diameter $OD_S$ may enlarge around the electrode 20″″, in an embodiment. Alternatively, the shaft 84 may maintain a substantially constant outer diameter $OD_S$.

In an embodiment, the configuration of the shaft 84 and electrode 20″″ shown in FIG. 8 may be manufactured through a swaging procedure. Accordingly, an electrode 20′, 20″, 20‴ according to any of the embodiments of FIGS. 5A-7B may be provided, then swaged. Alternatively, an electrode as known in the art may be provided, then swaged. Additional or alternatively, another process other than swaging may be used.

In an embodiment, an electrode may be configured with a rounded outer surface (e.g., as illustrated in FIG. 8) having a curvature that is similar to a curvature of a portion of a device on or in which the electrode is disposed. For example, a ring electrode may be disposed on a spine of a basket assembly (e.g., as shown in FIG. 2). In an embodiment, for example, an electrode disposed on a spine of a basket assembly may be configured with an outer surface that has a curvature consistent with the curvature of the spine when the basket assembly is expanded. In other embodiments, the outer surface of an electrode may be configured with a curvature to match the intended or anticipated curvature of a shaft portion or other feature of an elongate medical device.

The atraumatic electrode features illustrated in FIGS. 5A-8 and described above (e.g., rounded edges, partial chamfer, full chamfer, continuously-variable thickness or outer diameter) may be used for both ends of an electrode or for a single end of an electrode. Two or more of the features shown separately in FIGS. 5A-8 may be combined in a single electrode, in an embodiment. Furthermore, the atraumatic features are not limited to use with annular electrodes 20. Instead, the atraumatic features may be applied to a different type of electrode (e.g., the proximal end of a tip electrode 18, see FIG. 1) and/or to a non-electrode device.

Any of the atraumatic electrode features of FIGS. 5A-8 may be provided to improve the atraumatic properties of one or more electrodes on a catheter, introducer, other elongate medical device, or other device. The electrode embodiments of FIGS. 5A-8 may also simplify the manufacturing and assembly process, in embodiments. For example, in some known assemblies, electrodes may be covered by adhesive to create an atraumatic edge, and the adhesive may then be cured. The procedures of applying the adhesive and curing the adhesive may be both labor-intensive and time-consuming. Accordingly, providing one or more of the electrode embodiments of FIGS. 5A-8 may simplify and shorten the manufacture and assembly of an elongate medical device shaft or other device.

Figure 9:
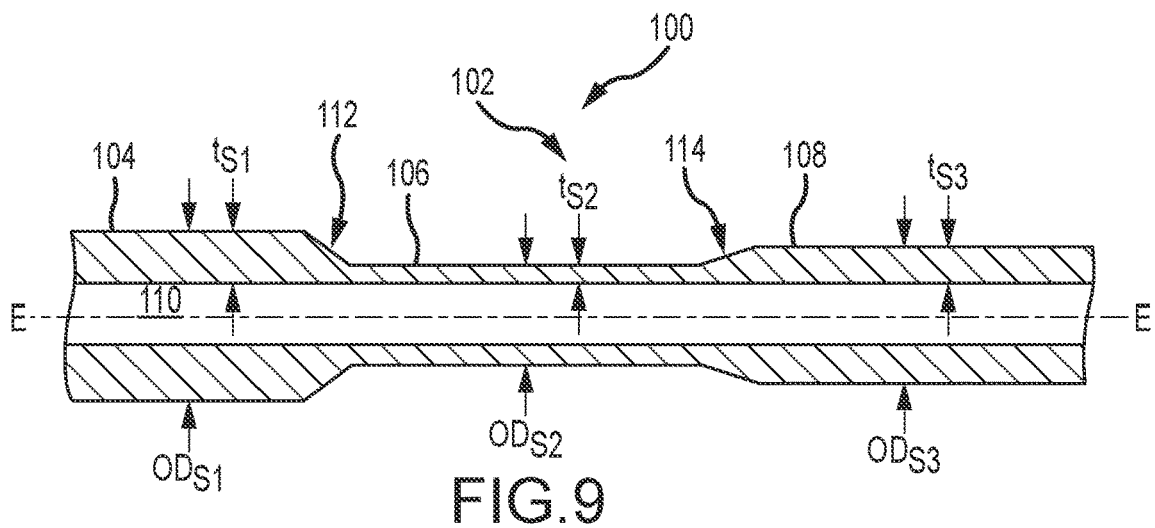
FIG. 9 is a diagrammatic view of a deflectable portion of an exemplary embodiment of an elongate medical device shaft having a variable outer diameter.

FIG. 9 is a diagrammatic view of a cross-sectional profile of an exemplary portion of an elongate medical device shaft 100 such as, for example, a deflectable portion 102. For example, the deflectable shaft portion 102 may be included in the catheter 10 of FIG. 1, the basket catheter 30 of FIG. 2, the introducer 38 of FIG. 3, or any other elongate medical device. The deflectable shaft portion 102 may define a longitudinal axis E and may have a plurality of axial portions. For example, the deflectable shaft portion may include three axial portions 104, 106, 108. A first axial shaft portion 104 may have a first thickness $t_{S1}$ and a first outer diameter $OD_{S1}$, a second axial shaft portion 106 may have a second thickness $t_{S2}$ and a second outer diameter $OD_{S2}$, and a third axial shaft portion 108 may have a third thickness $t_{S3}$ and a third outer diameter $OD_{S3}$. In an embodiment, the first axial portion 104 may have the largest outer diameter $OD_{S1}$ and thickness $t_{S1}$ of the three axial portions 104, 106, 108, the second axial portion 106 may have the smallest outer diameter $OD_{S2}$ and thickness $t_{S2}$ of the three axial portions 104, 106, 108, and the third axial portion 108 may have an outer diameter $OD_{S3}$ and thickness $t_{S3}$ that are between the first and second in size (i.e., in an embodiment, $t_{S1} > t_{S3} > t_{S2}$ and $OD_{S1} > OD_{S3} > OD_{S2}$). In an embodiment, the first axial portion 104 may be the most proximal of the three axial portions 104, 106, 108, the third axial portion 108 may be the most distal of the three axial portions 104, 106, 108, and the second axial portion 106 may be axially between the first and third axial portions 104, 108.

It should be understood that the term "deflectable portion" is used herein to refer to a portion of an elongate medical device shaft that is configured to achieve a desired shape or curvature responsive to an operator-applied or machine-applied force (e.g., through a deflection wire and pull ring coupled with the shaft). Although particular features of medical device shafts are described herein with reference to deflectable portions of the shaft, it should be understood that the techniques and configurations illustrated and described herein are not limited to use in deflectable portions of a shaft, but instead may be used in other portions of a shaft, in embodiments.

The different outer diameters $OD_{S1}$, $OD_{S2}$, $OD_{S3}$ of the three axial portions 104, 106, 108 may be created by using different thicknesses of polymer in a layer of the shaft 100, in an embodiment. For example, in the outermost polymer layer of the shaft 100, a thickest outer polymer layer of the three axial portions 104, 106, 108 may be used in the first axial portion 104, a thinnest outer polymer layer of the three axial portions 104, 106, 108 may be used in the second axial portion 106, and an intermediate outer polymer layer may be used in the third axial portion 108.

In an exemplary, non-limiting embodiment, the first axial portion 104 may have an outer diameter $OD_{S1}$ of about 0.100 inches, the second axial portion 106 may have an outer diameter $OD_{S2}$ of about 0.096 inches, and the third axial portion 108 may have an outer diameter $OD_{S3}$ of about 0.098 inches. The outer diameter $OD_{S1}$ of the first axial portion 104 may extend to the proximal end portion of the shaft 100, in an embodiment. The outer diameter $OD_{S3}$ of the third axial portion 108 may extend to the distal end portion of the shaft 100, in an embodiment.

The three axial portions 104, 106, 108 of the deflectable portion 102 of the shaft 100 may include structural features including one or more polymer layers (e.g., melt-processing polymers, such as PEBAX, commercially available from Arkema, Inc. or PELLETHANE, commercially available from Lubrizol Corporation, polyimide, and other appropriate polymers) one or more metal or other reinforcement structures (e.g., in the form of a braid or mesh), and other appropriate structural features. The deflectable shaft portion 102 may define one or more lumens 110 for fluid, deflection wires, electrical infrastructure, other medical devices, etc.

In an embodiment, as noted above, the different outer diameters $OD_{S1}$, $OD_{S2}$, $OD_{S3}$ may be manufactured by different thicknesses of melt-processing polymers. In an embodiment, different segments of polymer may be placed on a mandrel or on a more interior structure of the deflectable shaft portion 102 and subject to a reflow lamination process. The reflow process may cause the polymer segments to join as a unitary structure. The reflow process may also result in a gradual transition from the outer diameter of one axial portion 104, 106, 108 to the outer diameter of a neighboring axial portion 104, 106, 108, in an embodiment. As a result, the outer diameter of the finished deflectable shaft portion may taper from one axial portion 104, 106, 108 to another, rather than abruptly transition. Thus, as shown in FIG. 9, a first transition region 112 may taper from the first axial portion 104 to the second axial portion 106, and a second transition region 114 may taper from the third axial portion 108 to the second axial portion 106.

The deflectable shaft portion 102 may be disposed proximally of a distal end portion of a shaft of a catheter, introducer, or other elongate medical device, in an embodiment. In another embodiment, the deflectable shaft portion 102 may comprise a portion of such a distal end portion. Accordingly, the deflectable shaft portion 102 may be configured to accommodate one or more sensors such as, but not limited to, one or more of the electrodes illustrated in FIGS. 1, 2, and 4-8.

The deflectable shaft portion 102 may be configured, as its name suggests, to be deflected. Accordingly, the deflectable shaft portion 102, and/or a portion of the elongate medical device shaft 100 that is proximal or distal of the deflectable shaft portion 102, may be configured to accommodate one or more deflection elements, such as pull rings, shape wires, etc.

The different outer diameters $OD_{S1}$, $OD_{S2}$, $OD_{S3}$ and thicknesses $t_{S1}$, $t_{S2}$, $t_{S3}$ of the deflectable shaft portion 102 may provide both performance and manufacturing benefits. Performance benefits relative to other shaft configurations may include reduced force required for deflection, improved durability (i.e., after numerous deflections), improved curve shape, and improved planarity. For example, the larger outer diameter $OD_{S1}$ of the first axial portion 104 may contribute to improved durability and improved curve shape and the smaller axial diameter $OD_{S2}$ of the second axial portion 106 may contribute to reduced deflection force and improved planarity. Manufacturing benefits may include increased materials and space (e.g., in the third axial portion 108) for incorporation of additional components, such as sensors.

Figure 10A:
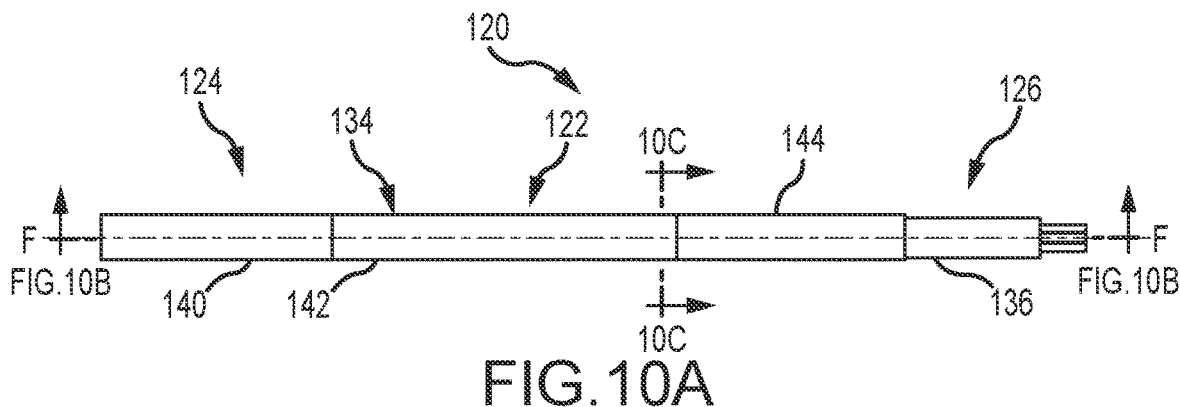
FIG. 10A is a plan view of a portion of an exemplary embodiment of an elongate medical device shaft having an axially-variable and radially-variable stiffness.
Figure 10B:
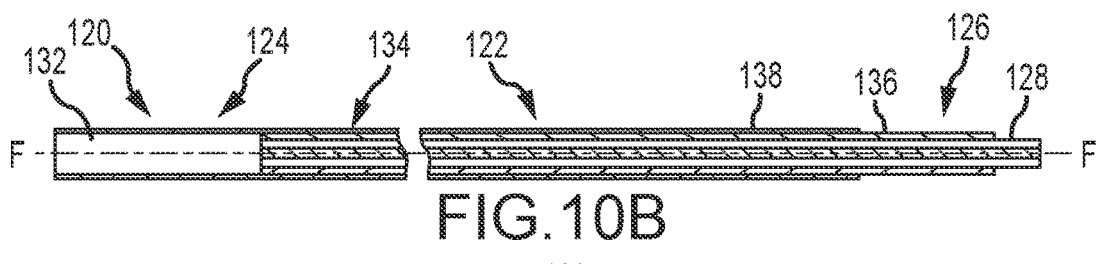
FIGS. 10B and 10C are cross-sectional views of the elongate medical device shaft portion of FIG. 10A.
Figure 10C:
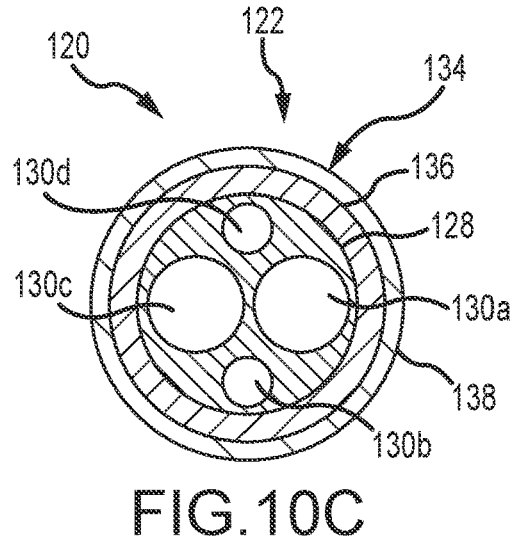

FIG. 10A is a plan view of an embodiment of an elongate medical device shaft 120. FIG. 10B is a longitudinal cross-sectional view of the shaft 120, taken along line 10B-10B in FIG. 10A. FIG. 10C is a radial cross-sectional view of a deflectable portion 122 of the shaft 120, taken along line 10C-10C in FIG. 10A. Referring to FIGS. 10A-10C, the shaft 120 may include a distal end portion 124, an intermediate deflectable portion 122, and a proximal end portion 126. The shaft may define a longitudinal axis F.

The shaft 120 may include a contiguous internal structure 128 that is generally cylindrical, in an embodiment. The internal structure 128 may define one or more longitudinal lumens. In an exemplary embodiment, the internal structure may define four lumens 130a, 130b, 130c, 130d (which may be referred to individually as a lumen 130 or collectively as the lumens 130). The internal structure 128 may comprise one or more materials including, but not limited to, polyimide and/or PEBAX of a suitable durometer (i.e., stiffness). For example, in an embodiment, the internal structure 128 may be or may include extruded polyimide.

The lumen(s) 130 of the internal structure may be provided for a variety of purposes. In an exemplary embodiment, a first lumen (e.g., lumen 130a) may be provided for irrigation fluid (e.g., in an embodiment in which the shaft 120 is included in an ablation catheter) and a second lumen (e.g., lumen 130c) for extending electrical wiring and other electrical infrastructure from the proximal end of the device (e.g., from an electromechanical connector in a handle) to sensors and other electrical elements in or on the distal end portion of the shaft. Third and fourth lumens (e.g., lumens 130b, 130d) may be provided, for example, for extending deflection wires, shape memory wires, and other elements for deflecting or guiding the shaft 120.

The shaft 120 may define a distal pocket, in an embodiment. The distal pocket may be configured, in an embodiment, to receive an electrode assembly, other sensor, and/or other diagnostic or interventional device.

The shaft 120 may further include an outer tube 134, radially-outward of the inner cylindrical structure 128, comprising a number of radial layers and a number of axial segments. In an embodiment, the inner tube may comprise a first radial layer 136 and a second radial layer 138. The first layer 136 may comprise one or more axial segments. In an embodiment, the first layer may comprise a single axial layer (i.e., a substantially unitary structure having substantially contiguous material properties). For example, the first layer may comprise a single melt-processing polymer of a suitable durometer and having a suitable thickness, in an embodiment. In an alternative embodiment, the first layer may comprise two or more melt-processing polymers in axially-adjacent segments having different durometers, thicknesses, etc.

The second layer of the tube may similarly comprise one or more axial segments. In an embodiment, the second layer may comprise two or more melt-processing polymers in axially-adjacent segments having different durometers, thicknesses, etc. For example, the second layer may include three different axial portions 140, 142, 144, in an embodiment—a first axial portion 140 in the distal end portion 124 of the shaft, a second axial portion 142 in the deflectable portion 122 of the shaft, and a third axial portion 144 in the proximal end portion 126 of the shaft.

The inner cylindrical structure 128 and outer tube 134 of the shaft 120 may comprise one or more polymers, in an embodiment. For example, as noted above, the inner cylindrical structure 128 may comprise polyimide. The layers of the outer tube 134 may comprise one or more melt-processing polymers, such as PEBAX or PELLETHANE. The shaft 120 may further include additional structural elements and features such as, for example and without limitation, one or more wire braid or mesh layers.

In an embodiment, one or more portions of the shaft 120 may have a radially-stratified stiffness. For example, but without limitation, the inner cylindrical structure 128 and the outer tube 134 may be configured such that the stiffness of one or more portions of the shaft 120 increases with each radially-outward layer. For example, in the deflectable portion 122 of the shaft 120, the inner cylindrical structure 128 may have a relatively highest stiffness (e.g., polyimide having a durometer of about 90D), the first layer 136 of the outer tube 134 may have a relatively intermediate stiffness (e.g., PELLETHANE having a durometer of about 55D), and the second layer 138 of the outer tube 134 may have a relatively lower stiffness (e.g., a PELLETHANE blend having a durometer of about 90AE/55D). That is, the stiffness of the inner cylindrical structure 128 may be higher than the stiffness of either layer 136, 138 of the outer tube 134, and the stiffness of the first layer 136 of the outer tube 134 may be higher than the stiffness of the second layer 138 of the outer tube 134. Furthermore, in an embodiment, additional radial layers may be included in one or more portions of the shaft 120, with each additional layer having a lower stiffness than the layer to its radial interior and/or a higher stiffness than the layer to its radial exterior.

The configuration of the shaft 120 may provide numerous operational advantages over other elongate medical device shafts. For example, a radially-increasing stiffness in the deflectable portion 122 of the shaft 120 may reduce the force required to deflect the deflectable portion 122 and may increase the distribution of stress radially, reducing the risk of delamination and kinking. Furthermore, a contiguous inner cylindrical structure 128 may provide resistance to joint failure and may reduce concentrated stress because the cylindrical inner structure 128 may lack joints.

In an embodiment, the features, including (but not limited to) an axially-varying thickness and outer diameter, illustrated in and described with respect to FIG. 9 may be applied to a catheter shaft in conjunction with the features, including (but not limited to) a radially-varying stiffness and contiguous inner cylindrical structure, illustrated in and described with respect to FIG. 10 in a single medical device. Furthermore, the atraumatic electrode features illustrated in and described with respect to one or more of FIGS. 5A-8 may be combined with the shaft features of FIGS. 9 and/or 10 in a single medical device.

FIG. 11 is a plan view of a portion 180 of an exemplary embodiment of a catheter. A full description of the catheter portion 180 and its various features may be found in U.S. patent application Ser. No. 13/836,846, filed Mar. 15, 2013, which is hereby incorporated by reference in its entirety. A brief description of the catheter portion 180 follows.

The catheter portion 180 may include a shaft 182 having a deflectable catheter shaft section 184, an intermediate catheter shaft section 186, and a proximal catheter shaft section (not shown in FIG. 11, but the proximal catheter shaft section, if present, may abut the right longitudinal end, as oriented in FIG. 11, of the intermediate catheter shaft section 186). In an embodiment, a shaft coupler 188 may be used for coupling the proximal catheter shaft section to the intermediate catheter shaft section 186. Similarly, a second shaft coupler (not shown) may be used for coupling the intermediate catheter shaft section 186 to the deflectable catheter shaft section 184.

The catheter shaft 182 may further include a number of electrodes, including a tip electrode 190 and three ring electrodes $20_1$, $20_2$, $20_3$. The tip electrode 190 may be a flexible tip electrode, such as that used in the Therapy™ Cool Flex™ ablation catheter manufactured by St. Jude Medical, Inc. of St. Paul, Minn. Additional details regarding a flexible tip electrode may be found in, for example, U.S. Pat. No. 8,187,267 B2 and United States patent application publication no. US 2010/0152731 A1, each of which is hereby incorporated by reference as though fully set forth herein. The ring electrodes $20_1$, $20_2$, $20_3$ may have features substantially as described throughout this disclosure including, but not limited to, one or more of the features illustrated in and described with respect to FIGS. 5A-8.

In an embodiment, the tip electrode 190 may have a length $L_{te}$ and may be separated from the distal-most ring electrode $20_1$ by a first spacing distance $S_1$. The distal-most ring electrode $20_1$ may be separated from the second most distal ring electrode $20_2$ by a second spacing distance $S_2$, and the second most distal ring electrode $20_2$ may be separated from the third most distal ring electrode $20_3$ by a third spacing distance $S_3$. In an embodiment, for example only, $L_{te}$ may be about 4 millimeters. In embodiments, $S_1$, $S_2$, and $S_3$ may have values between about 0.5 millimeters and about 5 millimeters or more, for example only. In an embodiment, the values of $S_1/S_2/S_3$, in millimeters, may be 0.9/0.9/0.9, 1/1/1, or 0.9/4/1.

Values of $S_1$, $S_2$, $S_3$, and other spacing distances listed herein may represent ideal, designed, or intended spacing values. Actual, as-manufactured spacing values may differ from the ideal by a certain tolerance amount. For example, in an embodiment, spacing values may have a tolerance of 0.4 millimeters—i.e., such that an intended or designed spacing value of one (1) millimeter may actually be between 0.6 millimeters and 1.4 millimeters. In another embodiment, spacing values may have a tolerance of about 0.3 millimeters. In another embodiment, spacing values may have a tolerance of about 0.2 millimeters. In another embodiment, spacing values may have a tolerance of about 0.1 millimeters.

The values of $L_{te}$, $S_1$, $S_2$, and $S_3$, as well as the values for spacing between additional electrodes and the dimensions of electrodes, included on an embodiment of a catheter or other elongate medical device, may be selected in accordance with the intended use of the device or to achieve desired characteristics in the device. For example, the spacing between a tip electrode and a ring electrode may be selected to achieve a particular voltage differential in a bipolar electrogram or other signal.

The elongate medical devices, and components thereof, illustrated and described herein may operate with a variety of medical device systems such as visualization systems, mapping systems, and navigation support and positioning systems (i.e., for determining a position and orientation (P&O) of a flexible elongate member or other medical device). One such system is illustrated in FIG. 12.

Figure 12:
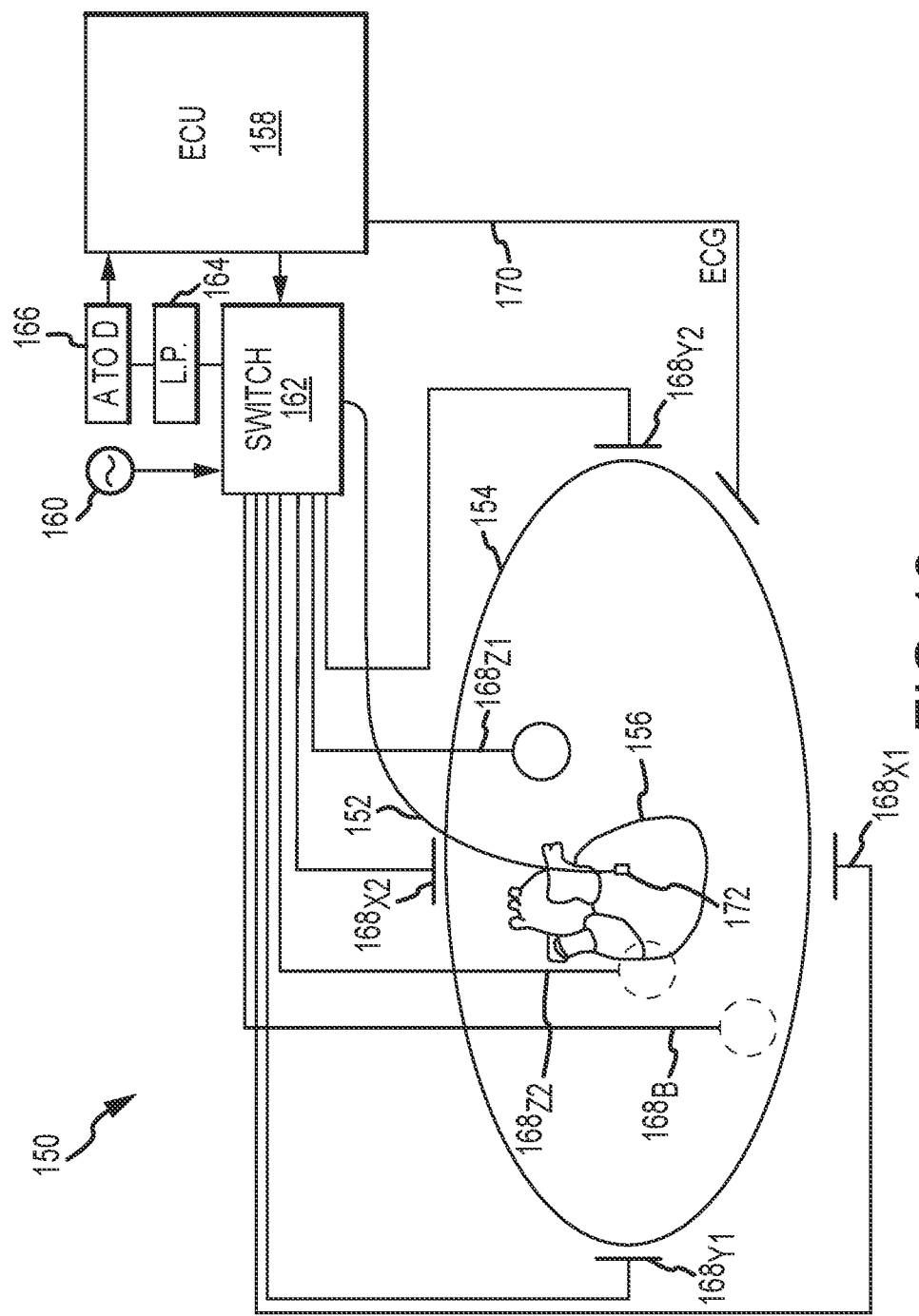
FIG. 12 is a schematic and diagrammatic view of an embodiment of a medical device mapping and navigation system.
Figure 13A:
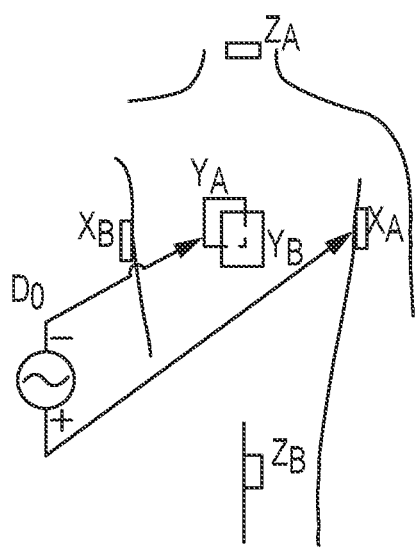
FIGS. 13A-13D are diagrammatic views of exemplary dipoles created using the mapping and navigation system of FIG. 12.
Figure 13B:
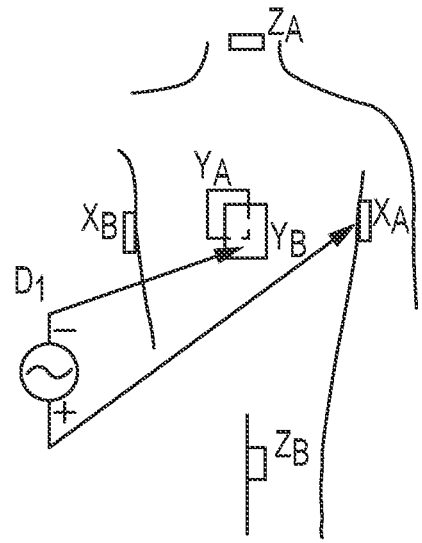
Figure 13C:
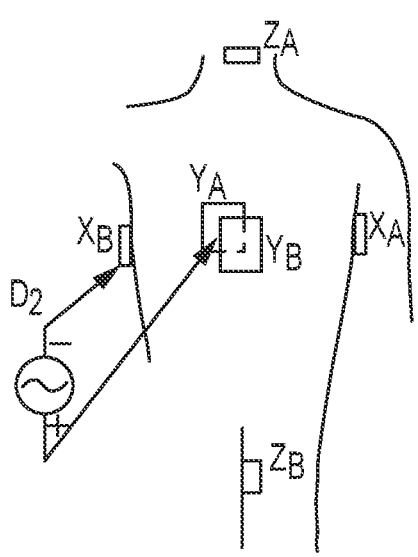
Figure 13D:
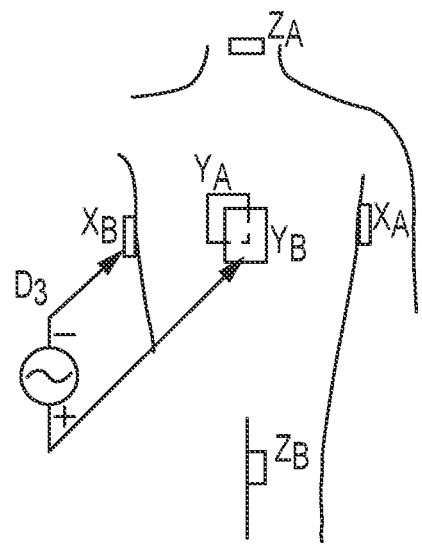

FIG. 12 is a schematic and diagrammatic view of an embodiment of a medical device mapping and navigation system 150. The system 150 is coupled with an elongate medical device 152 that can be guided to and disposed in a portion of a body 154, such as a heart 156. The medical device 152 can include one or more sensors 172 (which may be one or more of the electrodes 20, 20', 20'', 20''', 20'''', see FIGS. 1, 2 and 4-8) for, e.g., collecting electrophysiology data, applying ablation energy, and/or determining a location of the medical device 152 within the body 154. The system 150 may include, at least in part, an electronic control unit (ECU) 158, a signal generator 160, a switch 162, a low-pass filter 164, an analog-to-digital (A-to-D) converter 166, a plurality of body surface electrode patches $168_B$, $168_{X1}$, $168_{X2}$, $168_{Y1}$, $168_{Y2}$, $168_{Z1}$, $168_{Z2}$, and electrocardiogram (ECG) patches 170.

The system 150 may be provided for visualization, mapping, and/or navigation of internal body structures and may be referred to herein as "the navigation system." The navigation system 150 may comprise an electric field-based system, such as, for example, an EnSite™ Velocity™ cardiac electro-anatomic mapping system running a version of EnSite™ NavX™ navigation and visualization technology software commercially available from St. Jude Medical, Inc., of St. Paul, Minn. and as also seen generally by reference to U.S. Pat. Nos. 7,263,397 and 7,885,707, both hereby incorporated by reference in their entireties as though fully set forth herein. In other exemplary embodiments, the navigation system 150 may comprise systems other than electric field-based systems. For example, the navigation system 150 may comprise a magnetic field-based system such as the Carto™ system commercially available from Biosense Webster, and as generally shown with reference to one or more of U.S. Pat. Nos. 6,498,944; 6,788,967; and 6,690,963, the disclosures of which are hereby incorporated by reference in their entireties as though fully set forth herein. In another exemplary embodiment, the navigation system 150 may comprise a magnetic field-based system based on the MediGuide™ technology available from St. Jude Medical, Inc., and as generally shown with reference to one or more of U.S. Pat. Nos. 6,233,476; 7,197,354; and 7,386,339, the disclosures of which are hereby incorporated by reference in their entireties as though fully set forth herein. In yet another embodiment, the navigation system 150 may comprise a combination electric field-based and magnetic field-based system, such as, for example and without limitation, the system described in pending U.S. patent application Ser. No. 13/231,284, or the Carto™ 3 system commercially available from Biosense Webster, and as generally shown with reference to U.S. Pat. No. 7,536,218, the disclosures of which are hereby incorporated by reference in their entireties as though set fully forth herein. In yet still other exemplary embodiments, the navigation system 150 may comprise or be used in conjunction with other commonly available systems, such as, for example and without limitation, fluoroscopic, computed tomography (CT), and magnetic resonance imaging (MRI)-based systems. For purposes of clarity and illustration only, the navigation system 150 will be described hereinafter as comprising an electric field-based system, such as, for example, the EnSite™ NavX™ system identified above.

The medical device 152 and associated sensors 172 may be provided for a variety of diagnostic and therapeutic purposes including, for example, electrophysiological studies, pacing, cardiac mapping, and ablation. In an embodiment, the medical device can be an ablation catheter (e.g., the catheter 10 of FIG. 1), mapping catheter (e.g., the basket-style catheter 30 of FIG. 2), introducer (e.g., the introducer 38 of FIG. 3), or other elongate medical device. The number, shape, orientation, and purpose of the sensors 172 may vary in accordance with the purpose of the catheter 10. In an embodiment, at least one sensor 172 can be an electrode. For purposes of illustration, the description below will be with respect to an embodiment in which the sensors 172 comprise one or more electrodes (i.e., an electrode 172), but the disclosure is not limited to such an embodiment.

With the exception of the patch electrode $168_B$ called a "belly patch," the patch electrodes 168 are provided to generate electrical signals used, for example, in determining the position and orientation of the medical device 152 and in the guidance thereof. In one embodiment, the patch electrodes 168 are placed generally orthogonally on the surface of the body and are used to create axes-specific electric fields within the body. For instance, in one exemplary embodiment, patch electrodes $168_{X1}$, $168_{X2}$ may be placed along a first (x) axis. Patch electrodes $168_{Y1}$, $168_{Y2}$ may be placed along a second (y) axis, and patch electrodes $168_{Z1}$, $168_{Z2}$ may be placed along a third (z) axis. Each of the patch electrodes 168 may be coupled to the multiplex switch 162. In an exemplary embodiment, the ECU 158 may be configured, through appropriate software, to provide control signals to the multiplex switch 162 to thereby sequentially couple pairs of patch electrodes 168 to the signal generator 160. Excitation of each pair of electrodes 168 (e.g., in either orthogonal or non-orthogonal pairs) generates an electrical field within the patient's body 154 and within an area of interest, such as the heart 156. Voltage levels at non-excited electrodes 168, which are referenced to the belly patch $168_B$, are filtered by the low-pass filter 164 and converted by the A-to-D converter 166 and provided to the ECU 158 for use as reference values.

In an exemplary embodiment, the electrode 172 comprises a positioning electrode and is configured to be electrically coupled to the ECU 158. With a positioning electrode 172 electrically coupled to the ECU 158, the positioning electrode 172 may be placed within electrical fields created in the body 154 (e.g., within the heart 156) by exciting the patch electrodes 168. The positioning electrode 172 experiences voltages that are dependent on the position of the positioning electrode 172 relative to the locations of the patch electrodes 168. Voltage measurement comparisons made between the positioning electrode 172 and the patch electrodes 168 may be used to determine the position of the positioning electrode 172 relative to the heart 156 or other tissue. Movement of the positioning electrode 172 proximate a tissue (e.g., within a chamber of the heart 156) may produce information regarding the geometry of the tissue. This information may be used, for example, to generate models and maps of anatomical structures. Such maps and models may reflect a particular state of the anatomical structure such as, for example, the shape of the heart at a particular point in the cardiac cycle. Position information determined according to measurements made with the positioning electrode 172 may thus be associated with a particular portion of the cardiac cycle based on readings from the ECG patches 170. Information received from the positioning electrode 172 can also be used to display on a display device, the location and orientation of the positioning electrode 172 and/or a portion of the medical device 152 relative to the heart 156 or other tissue. Accordingly, among other things, the ECU 158 of the navigation system 150 may provide a means for generating display signals used to control a display and the creation of a graphical user interface (GUI) on the display.

The ECU 158 may comprise a programmable microprocessor or microcontroller, or may comprise an application specific integrated circuit (ASIC). The ECU 158 may include a an input/output (I/O) interface through which the ECU 158 may receive a plurality of input signals including, for example, signals generated by patch electrodes 168 and the positioning electrode 172 (among others), and generate a plurality of output signals including, for example, those used to control a display and other user interface components. The ECU 158 may be configured to perform various functions with appropriate programming instructions or code (i.e., software). Accordingly, the ECU 158 can be programmed with one or more computer programs encoded on a computer-readable storage medium for performing functionality described herein.

FIGS. 13A-13D show a plurality of exemplary non-orthogonal dipoles, designated $D_0$, $D_1$, $D_2$ and $D_3$. Referring to FIGS. 12 and 13A-13D, for any desired axis, the potentials measured across an intra-cardiac positioning electrode 172 resulting from a predetermined set of drive (source-sink) configurations may be combined algebraically to yield the same effective potential as would be obtained by simply driving a uniform current along the orthogonal axes. Any two of the patch electrodes 168 may be selected as a dipole source and drain with respect to a ground reference, e.g., belly patch $168_B$, while the unexcited body surface electrodes 168 measure voltage with respect to the ground reference $168_B$. The positioning electrode 172 placed in the heart 156 is also exposed to the field from a current pulse and is measured with respect to ground, e.g., the belly patch $168_B$. In practice, a medical device 152 or multiple medical devices 152 within the heart 156 may contain multiple positioning electrodes 172 and each positioning electrode potential may be measured separately.

Data sets from each of the patch electrodes 168 and the positioning electrode 172 may be used to determine the location of the positioning electrode 172 within the heart 156. After the voltage measurements are made, a different pair of surface electrodes 168 is excited by the signal generator 160 and the voltage measurement process of the remaining patch electrodes 168 and positioning electrode 172 takes place. The sequence occurs rapidly, e.g., on the order of 100 times per second, in an embodiment. To a first approximation, the voltage on the positioning electrode 172 within the heart 156 bears a linear relationship with position between the patch electrodes 168 that establish the field within the heart 156, as more fully described in U.S. Pat. No. 7,263,397 referred to above.

In summary, FIG. 12 shows an exemplary navigation system 150 that employs seven body surface electrodes (patches) 168, which may be used for injecting current and sensing resultant voltages. Current may be driven between two patches 168 at any time; some of those driven currents are illustrated in FIGS. 13A-13D. Measurements may be performed between a non-driven patch 168 and, for example, the belly patch $168_B$ as a ground reference. A patch bio-impedance, also referred to as a "patch impedance" may be computed according to the following equation:

$$BioZ[c \to d][e] = \frac{V_e}{I_{c \to d}} \quad (1)$$

where $V_e$ is the voltage measured on patch e and $I_{c \to d}$ is a known constant current driven between patches c and d, where patches c, d, and e may be any of the patch electrodes 168. The position of a positioning electrode 172 may be determined by driving current between different sets of body patches 168 and measuring one or more patch impedances along with the voltage on the positioning electrode 172. In one embodiment, time division multiplexing may be used to drive and measure all quantities of interest. Position determining procedures are described in more detail in U.S. Pat. Nos. 7,263,397 and 7,885,707 referred to above, as well as other references.

Although a number of embodiments have been described above with a certain degree of particularity, those skilled in the art could make numerous alterations to the disclosed embodiments without departing from the spirit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. An elongate medical device assembly comprising:
an elongate shaft body having an outer diameter; and
an annular electrode configured to deliver ablative energy, the annular electrode disposed on the elongate shaft body, the annular electrode defining a longitudinal axis and having an outer diameter and an inner diameter, wherein the outer diameter is greater at an axial center of the annular electrode than at an axial end of the annular electrode;
wherein the outer diameter of the axial end of the annular electrode is radially within the outer diameter of the elongate shaft body and wherein at least a portion of the outer diameter of the elongate shaft body enlarges around a portion of the annular electrode.

2. The elongate medical device assembly of claim 1, wherein the outer diameter of the annular electrode is greater at the axial center than at either axial end of the annular electrode.

3. The elongate medical device assembly of claim 1, wherein the annular electrode defines a thickness between the outer diameter and an inner diameter, wherein the thickness is about 25% to about 75% less at the axial end than at the axial center.

4. The elongate medical device assembly of claim 1, wherein the axial end of the annular electrode comprises a chamfer.

5. The elongate medical device assembly of claim 1, wherein the outer diameter of the annular electrode has a continuous curvature.

6. The elongate medical device assembly of claim 1, wherein the annular electrode is configured to deliver at least one of radiofrequency ablative energy and high intensity focused ultrasound ablative energy.

7. The elongate medical device assembly of claim 1, wherein the elongate shaft body comprises a plurality of flexible spines, and wherein the annular electrode is disposed on at least one of the plurality of spines.

8. An elongate medical device assembly comprising:
an elongate shaft body comprising:
an inner cylindrical structure defining a longitudinal lumen and defining a longitudinal axis; and
an outer tube, disposed radially-outward of the inner cylindrical structure, comprising a first radial layer and a second radial layer that is radially-outward of the first radial layer, the first radial layer having a different stiffness than the second radial layer;
wherein the inner cylindrical structure and the outer tube comprise an intermediate axial portion of the elongate shaft body, wherein the elongate shaft body further comprises:
a distal end portion, axially-distal of the intermediate axial portion; and
an annular electrode configured to deliver ablative energy and disposed on the distal end portion, the annular electrode having an outer diameter, wherein the outer diameter is greater at an axial center of the annular electrode than at an axial end of the annular electrode; and
wherein the elongate shaft body has an outer diameter, wherein the outer diameter of the axial end of the annular electrode is radially within the outer diameter of the elongate body and wherein at least a portion of the outer diameter of the elongate shaft enlarges around a portion of the annular electrode.

9. The elongate medical device assembly of claim 8, wherein the second radial layer has a lower stiffness than the first radial layer.

10. The elongate medical device assembly of claim 8, wherein the second radial layer comprises a first axial section and a second axial section, the first axial section having a different stiffness than the second axial section.

11. The elongate medical device assembly of claim 8, wherein the first radial layer and the second radial layer have respective stiffnesses that are lower than a stiffness of the inner cylindrical structure.

12. The elongate medical device assembly of claim 8, wherein the inner cylindrical structure comprises polyimide.

13. The elongate medical device assembly of claim 8, wherein the first radial layer comprises a first melt-processed polymers and the second radial layer comprises a second melt-processed polymer.

14. The elongate medical device assembly of claim 8, wherein the inner cylindrical structure defines a plurality of longitudinally-extending lumens.

15. The elongate medical device assembly of claim 8, wherein the annular electrode is configured to deliver at least one of radiofrequency ablative energy and high intensity focused ultrasound ablative energy.

16. The elongate medical device assembly of claim 8, wherein the axial end of the annular electrode comprises a chamfer.

17. The elongate medical device assembly of claim 8, wherein the outer diameter of the annular electrode has a continuous curvature.

18. The elongate medical device assembly of claim 8, wherein the distal end portion of the elongate shaft body comprises a plurality of flexible spines, and wherein the annular electrode is disposed on at least one of the plurality of spines.

* * * * *